United States Patent
Swann

(10) Patent No.: US 9,309,811 B2
(45) Date of Patent: Apr. 12, 2016

(54) FUEL DELIVERY SYSTEM

(71) Applicant: ROLLS-ROYCE PLC, London (GB)

(72) Inventor: Peter Swann, Nottingham (GB)

(73) Assignee: ROLLS-ROYCE plc, London (GB)

( * ) Notice: Subject to any disclaimer, the term of this patent is extended or adjusted under 35 U.S.C. 154(b) by 0 days.

(21) Appl. No.: 14/486,337

(22) Filed: Sep. 15, 2014

(65) Prior Publication Data
US 2015/0100219 A1  Apr. 9, 2015

(30) Foreign Application Priority Data

Oct. 8, 2013 (GB) .................................. 1317731.6

(51) Int. Cl.
F02C 9/28 (2006.01)
F02C 3/20 (2006.01)
(Continued)

(52) U.S. Cl.
CPC ... *F02C 9/28* (2013.01); *F02C 3/20* (2013.01); *F02C 7/22* (2013.01); *F02C 9/40* (2013.01); *G01N 21/538* (2013.01); *F05D 2270/081* (2013.01); *F05D 2270/082* (2013.01)

(58) Field of Classification Search
CPC .......... B64C 2201/042; B64C 39/024; B64D 2041/005; B64D 2211/00; B64D 27/24; F02D 41/3094; F02M 37/0052; F02M 69/044; F02M 69/045; F02M 69/046; H01M 2008/1293; H01M 2250/20; H01M 8/04753; Y02E 60/50; Y02T 10/123; Y02T 50/44; Y02T 50/62; Y02T 50/69; Y02T 90/32; Y02T 90/36
USPC .......... 123/295, 456; 244/30, 53 R; 239/14.1; 137/2; 73/305; 60/39.23; 126/85 R; 429/423, 425
See application file for complete search history.

(56) References Cited

U.S. PATENT DOCUMENTS 3,289,409 A  12/1966 Schirmer
3,517,505 A  6/1970 Anderson et al.
(Continued)

FOREIGN PATENT DOCUMENTS

CN  102926874 A  2/2013
EP  2 677 138 A2  12/2013
(Continued)

OTHER PUBLICATIONS

May 9, 2014 Search Report issued in British Application No. 1317731.6.
(Continued)

*Primary Examiner* — James Trammell
*Assistant Examiner* — Sanjeev Malhotra
(74) *Attorney, Agent, or Firm* — Oliff PLC

(57) ABSTRACT

This invention concerns a fuel delivery system for an engine, in which two or more discrete fuel compositions are made available to the engine. The system has a vapor trail detection sensor configured to generate a detection signal indicative of a characteristic of a vapor trail. A regulator is configured to regulate a percentage of a first and a second fuel composition delivered to the engine as resultant fuel composition. A controller is arranged to undertake a search of trial fuel compositions by controlling the regulator to deliver to the engine a plurality of trial fuel compositions having different ratios of the first and second fuel compositions. The controller controls delivery of a resultant fuel composition to the engine in response to the vapor trail characteristic detection signals for said plurality of trial fuel compositions.

20 Claims, 8 Drawing Sheets

(51) Int. Cl.
*F02C 7/22* (2006.01)
*F02C 9/40* (2006.01)
*G01N 21/53* (2006.01)

(56) References Cited

U.S. PATENT DOCUMENTS

| | | | |
|---|---|---|---|
| 3,517,512 | A | 6/1970 | Anderson et al. |
| 4,766,725 | A | 8/1988 | Singh |
| 5,005,355 | A | 4/1991 | Singh |
| 2002/0007816 | A1* | 1/2002 | Zur Loye ................. F02B 1/04 123/295 |
| 2003/0205641 | A1* | 11/2003 | McElroy ............... B64C 39/024 244/53 R |
| 2003/0207164 | A1* | 11/2003 | McElroy ............... B64C 39/024 244/30 |
| 2006/0000452 | A1* | 1/2006 | Tokuda ................. F02D 33/006 123/456 |
| 2008/0072577 | A1 | 3/2008 | Taylor et al. |
| 2008/0295593 | A1* | 12/2008 | Yokoo ................. F02M 37/0029 73/305 |
| 2009/0013591 | A1 | 1/2009 | Bradin et al. |
| 2010/0043443 | A1 | 2/2010 | Noppel et al. |
| 2010/0122519 | A1 | 5/2010 | Epstein et al. |
| 2010/0132330 | A1 | 6/2010 | Noppel et al. |
| 2010/0252648 | A1* | 10/2010 | Robinson ................ A01G 15/00 239/14.1 |
| 2010/0288367 | A1* | 11/2010 | Pursifull .......... B60K 15/03006 137/2 |
| 2011/0225947 | A1* | 9/2011 | Lacy ......................... F23R 3/26 60/39.23 |
| 2012/0067341 | A1* | 3/2012 | Mateos Martin ....... F23N 1/005 126/85 R |
| 2013/0173074 | A1 | 7/2013 | Chandler |
| 2013/0316258 | A1* | 11/2013 | Tsukagoshi ....... H01M 8/04589 429/423 |
| 2013/0343958 | A1 | 12/2013 | Swann |
| 2015/0086888 | A1* | 3/2015 | Tsukagoshi ................ C01B 3/34 429/425 |

FOREIGN PATENT DOCUMENTS

| | | |
|---|---|---|
| EP | 2 677 139 A2 | 12/2013 |
| EP | 2 685 280 A2 | 1/2014 |
| WO | 2011029432 A1 | 3/2011 |

OTHER PUBLICATIONS

Jan. 16, 2015 Search Report issued in European Application No. 14184757.

* cited by examiner

FUEL DELIVERY SYSTEM

BACKGROUND OF THE INVENTION

The present invention relates to a machine fuel delivery system and method, typically, although not exclusively, for aircraft engines.

Vapour trails are artificial clouds that are visible trails of condensed water vapour exhausted by vehicles' engines. They may be formed as warm, moist exhaust gas mixes with ambient air, and arise from the precipitation of microscopic water droplets or, if the air is cold enough, tiny ice crystals. The term "vapour trails" is intended to refer both to condensation trails (that is to say "contrails") from aircraft and to water and/or ice precipitation in or attributable to the exhaust plumes from engines of other machines and vehicles, such as ships.

It may be undesirable for some ships to produce vapour trails in certain situations. For example, a military ship producing a vapour trail from its exhaust funnels is highly visible from the air and hence much easier to target.

It is understood that, depending on the timescale considered, the climate-warming impact of aircraft exhaust vapour trails and resulting vapour trail-cirrus may be of a magnitude similar to, or perhaps even greater than, that of the $CO_2$ emitted by aircraft, and therefore may represent a significant element of aviation's total climate impact. It is also understood that an aircraft vapour trail, once formed, will persist in ambient air which is supersaturated with respect to ice, leading to greater climate-warming impact as a result of the increase in longevity of the vapour trail.

US2010/0122519 describes the use of ultra-low sulphur aviation fuel as an alternative to conventional fuel to reduce sulphur by-product generation and hence reduce contrail formation. This document emphasises the need to retain the purity of the ultra-low sulphur aviation fuel, and hence the requirement to manage the supply chain which delivers the fuel, and to avoid mixing with other fuels.

The attempted suppression of vapour trail formation through the reduction of exhaust water vapour content through use of a heat exchanger and condenser arrangement (US2008072577A) potentially introduces significant weight into the engine. Furthermore, the weight penalty is incurred throughout the full duration of a flight, even though vapour trail suppression may only be required for a small percentage of the flight time.

Attempted suppression of vapour trail formation through the use of directed electromagnetic energy (US2010132330A) into the engine exhaust plume could incur a weight penalty. Furthermore, the energy required to operate the system could represent a significant portion of the engine power and thus incur a fuel-burn penalty. Further, in military applications, the emission of powerful electromagnetic radiation has the undesirable effect of increasing the aircraft's detectability.

Attempted suppression of vapour trail formation through the use of ultrasound directed into the engine exhaust plume (US2010043443A) may also incur a material weight penalty associated with equipment for generating the required sound levels.

The attempted modification or suppression of vapour trails through the use of chemicals (U.S. Pat. No. 5,005,355A, U.S. Pat. No. 4,766,725A, U.S. Pat. No. 3,517,505A, U.S. Pat. No. 3,517,512A, US2009013591A) injected either into the engine (whether with the fuel or separately from the fuel) or into the exhaust plume presents the prospect of additional pollution, incurs a weight penalty through the need to carry fuel additives with potentially little or no calorific value of their own (in comparison with conventional aviation fuel when burned within the engine), and may present challenges to engine reliability and/or component life.

The attempted hiding of vapour trails through introducing black carbon into the aircraft engine effluent (U.S. Pat. No. 3,289,409A) results in additional emissions of a species (black carbon) which is known to have an environmental warming impact.

The strategy of avoiding regions prone to vapour trail formation and/or persistence through the routing of aircraft around, above and/or below such regions has the disadvantage that it increases workload for air traffic control and/or pilots, reduces airspace capacity and, in the case of routing around regions prone to vapour trail formation or persistence (which can be tens or hundreds of kilometers in horizontal extent), the length of the route followed by the aircraft is increased, resulting in a fuel-burn penalty. Additionally in the case of climbing so as to fly above regions prone to vapour trail formation or persistence, additional fuel is burned to provide the increased thrust necessary to perform the climb. If aircraft are scheduled to fly below regions prone to vapour trail formation or persistence, additional fuel may be burned subsequently if the aircraft is to return to its optimal cruising altitude once the aircraft has passed the avoided region.

In the case either of climbing so as to fly above or of descending so as to fly below regions of air susceptible to vapour trail formation and/or persistence, the aircraft will be required to fly at an altitude that may differ from the optimal cruise altitude given the aircraft's current weight. In other words, the ability of the aircraft to follow an optimal cruise-climb trajectory is hindered by the requirement to change altitude so as to avoid the region of air susceptible to vapour trail formation and/or persistence.

It is understood that the climate warming impact of a vapour trail of a given horizontal extent is determined, at least in part, by its optical depth. Reductions in the number of soot particles emitted per unit mass of fuel burned by an aircraft's engine could reduce the initial optical depth of exhaust vapour trails. Hereafter in this application the number of soot particles emitted per unit mass of fuel burned is termed the "soot emission index".

Further, it is understood that the production of soot from engine exhausts can be reduced through the reduction or elimination of aromatic and/or other non-paraffinic content in the fuel used. Biofuels are typically low in aromatics and/or other non-paraffinics. However, biofuels are typically much more expensive than conventional fuels and are in extremely short supply. Hence it is undesirable to fuel a vehicle with biofuel throughout its period of operation, especially as the vehicle it powers may operate for much of its time in conditions where vapour trails will not form and/or persist regardless of the fuel used.

Hence a system which reduces the optical depth of young vapour trails, therefore potentially reducing their climate warming impact, whilst optimising the use of more expensive biofuels, is highly desirable.

BRIEF SUMMARY OF THE INVENTION

According to a first aspect of the invention there is provided a fuel delivery system for an engine, the system comprising a vapour trail detection sensor configured to generate a detection signal indicative of a characteristic of a vapour trail; a regulator configured to regulate a volume or percentage of a first and a second fuel composition delivered to the engine as resultant fuel composition; and a controller arranged to undertake a search of trial fuel compositions by controlling the regulator to deliver to the engine a plurality of trial fuel compositions having different ratios of the first and second fuel compositions and to control delivery of a resultant fuel composition to the engine in response to the vapour trail characteristic detection signals for said plurality of trial fuel compositions.

The engine may be a propulsion engine, such as an axial flow engine. The engine may be a gas turbine engine. The engine may be an aircraft engine.

The vapour trail detection sensor may comprise a plurality or array of sensors. The vapour trail detection sensor may comprise a vapour trail optical depth sensor. The vapour trail detection sensor may detect the presence/absence of a contrail.

The regulator may comprise a plurality of individual regulators. The regulator preferably comprises an individual regulator for each of the first and second fuel compositions. The regulator may comprise a plurality of regulator valves. The regulator may comprise an individual regulator valve for each of the first and second fuel compositions.

The system may further comprise one or more ambient condition sensor, such as an ambient temperature sensor or an ambient humidity sensor. The control unit may further comprise a combination of the aforementioned or other ambient condition sensors.

The controller may comprise machine readable instructions, such as a search algorithm, for implementing the search. The controller may instigate a search upon detection of a change, e.g. a material change, in an engine operating condition and/or an ambient condition. The controller may instigate the search on a condition that the change in condition meets or exceeds a predetermined duration and/or a predetermined magnitude, for example so as to represent a material change in condition.

The controller may instigate a search on condition that the sensed vapour trail characteristic meets or exceeds a predetermined threshold value, which may be a zero value.

The search performed by the controller may comprise a sweep through a range of ratios of the first and second fuel composition. The search may or may not comprise a continuous sweep through the range. The search may comprise identifying a plurality of discrete fuel compositions ratios over the range, or a subset of the range, and implementing delivery of trial fuel compositions at said discrete ratios.

The search may comprise setting a range of fuel composition ratios to be searched. The range may be a predetermined range or else a range calculated by the controller, for example under one or more prescribed or transient operating constraint of the engine. The range may comprise a maximum or minimum percentage of any one fuel composition or else may be determined by one or more threshold operational parameter for the engine.

The search may comprise a first or coarse search, in which the controller sweeps through a predetermined range of fuel ratios in a predetermined manner and subsequently determines the desirable final fuel composition ratio, or a desirable final fuel composition sub-range, within said range. For example the controller may analyse the vapour trail sensor feedback for the entire range after implementation of the sweep. This search may thus comprise a default search, which may be implemented in its entirety irrespective of the sensor feedback, whereby a desirable fuel composition ratio is determined only after the full range has been searched.

The search may comprise a second or fine search, in which the controller implements a first trial fuel composition ratio and awaits the feedback from the vapour detection sensor(s) for the first trial ratio, prior to implementing one or more further trial fuel composition ratio. The second/fine search may be implemented within a sub-range defined by the first/coarse search or else in response to a relatively small change in operating/ambient condition. The second search may comprise an optimisation routine. Thus the optimiser can explore individual points within a localised area of the total search space. The optimiser may incur a time delay between successive trial fuel composition ratios, such as a time delay sufficient to allow a contrail to form. The time delay incurred by the optimiser may comprise the time necessary for detection of the resulting change in vapour trail characteristic.

Any or a combination of the first and/or second searches may be used. The controller may comprise a first and/or second search algorithm, which may comprise a pre-search algorithm and/or optimisation algorithm. The pre-search algorithm may identify a sub-region of the available search space corresponding to lower environmental impact. The optimisation algorithm may be limited to a search within the identified sub-region for the optimum fuel blend. The combination of the pre-search and optimisation routines can provide for quicker convergence on an optimal fuel blend with minimal environmental impact.

The system may comprise one or more engine operation sensor. The controller may identify an engine operation regime based upon the engine operation sensor readings and/or ambient sensor readings. A plurality of regimes may be defined, each of which having a different predetermined relationship between an engine operation parameter and the vapour trail characteristic. The engine operation parameter may or may not comprise soot emission index. Optionally, a representation (e.g. database, lookup-table, decision-tree, algorithm etc) may be used/accessed by the controller, from which can be inferred the regime of engine operation (defined below).

The controller may only perform a search in response to a determination that the engine is operating in one or more of the plurality of regimes. For one or more further regimes, the controller may set a final fuel composition according to fuel ratio setting algorithm or according to a predetermined default fuel ratio.

The controller may or may not comprise a usage policy, for example defining the circumstances under which the system should or should not be employed. The controller may determine whether or not to implement a search based upon an engine operation regime as described above. Additionally or alternatively, the controller may decide whether or not to conduct a search based upon a relationship/mapping between fuel composition ratio and the engine operation parameter. The controller may have a default setting in which the search is performed.

The controller may select from within the searched range of fuel compositions a final fuel composition which offers a minimum value of the sensed vapour trail characteristic or else which meets a predetermined threshold vapour trail characteristic value, which may be a zero value. The controller may aim to minimise contrail optical depth.

The system may further comprise a plurality of fuel tanks (a tank being a single tank or alternatively a network of fluidly interconnected tanks) each tank being fluidly isolated from the other tank(s). A first fuel tank may comprise the first fuel composition and a second fuel tank may comprise the second fuel composition. One or more further fuel tank, comprising one or more further respective fuel composition, may be provided.

The system may comprise one or more fuel blender (e.g. one per engine) which is arranged to receive the first and second fuel compositions from the one or more regulator and to output the final fuel composition to the engine, typically to one or more engine fuel injector(s).

According to a second aspect of the invention, there is provided a data carrier comprising machine readable instructions for operation of an engine fuel delivery controller in accordance with the first aspect.

According to a third aspect of the invention, there is provided a method of delivery of fuel to an engine in accordance with the first aspect.

Any of the preferable features defined above in relation to the first aspect may be applied to the second or third aspect.

BRIEF DESCRIPTION OF THE DRAWINGS

Practicable embodiments of the invention are described in further detail below by way of example only with reference to the accompanying drawings, of which.

DETAILED DESCRIPTION OF THE INVENTION

Figure 1:
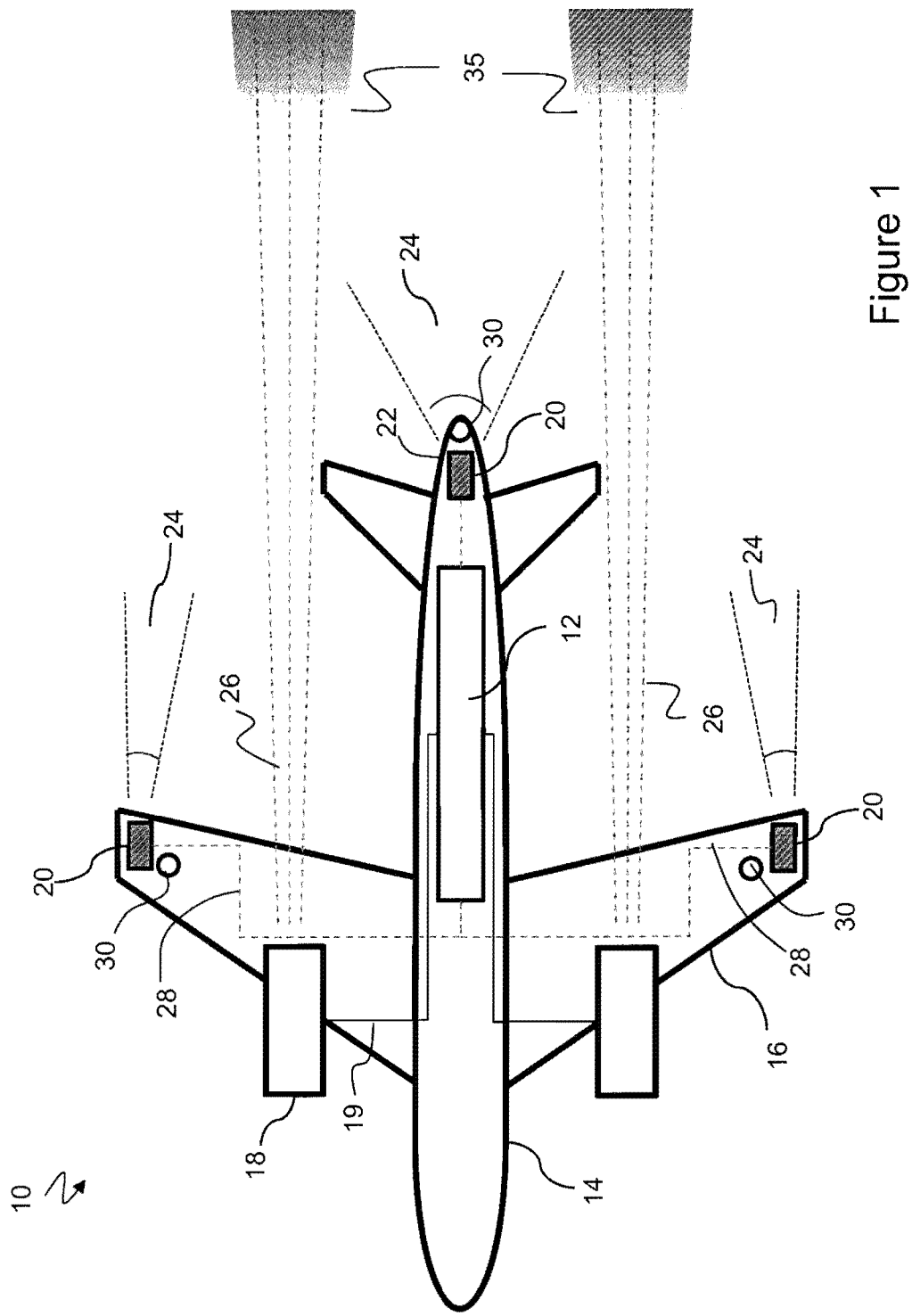
FIG. 1 shows a fuel system according to the present disclosure on an aircraft.

FIG. 1 shows a machine 10, in this example an aircraft, which comprises a fuel system 12 according to the present disclosure. In the example shown the aircraft comprises a fuselage 14 from which wings 16 extend, with engines 18 mounted to the wings. Other examples might involve alternative aircraft configurations, and different numbers of engines. The majority of the fuel system 12 is shown located in the fuselage 14. In alternative examples the fuel system 12 may be located elsewhere in the machine 10. Fuel pipes 19 fluidly connect the fuel system 12 and engines 18.

The fuel system 12 comprises at least one vapour trail detection sensor 20. In the example shown in FIG. 1, vapour trail detection sensors 20 are mounted towards the rear of the aircraft 10 facing aft. For example they are located at the tip of one or both wings 16 and/or at a trailing edge 22 of the fuselage. The, or each, vapour trail detection sensor 20 is mounted such that it has a field of view directed towards a vapour trail formation region. That is to say they are positioned such that they have a field of view 24 in a direction downstream of the vehicle 10, which in operation will offer a view of vapour trails 35 formed within the exhaust plumes 26 downstream of the engines 18. Each of the vapour trail detection sensors 20 is configured to generate a first signal 28 (shown as a dotted line) which indicates, for example, an optical depth (OD) of the young vapour trail 35.

Each vapour trail detection sensor 20 is an optical device configured to deliver a signal indicative of the presence and/or properties of a vapour trail 35. A source of illumination 30 may also be provided on the aircraft and directed towards at least one region downstream of the engines 18 to illuminate at least part of the field of view 24 of the sensor 20. The sensor 20 is configured to detect electromagnetic radiation of at least one wavelength emitted and/or reflected by the vapour trail in response to energy emitted from the source of illumination 30. In other embodiments, instead of illumination, an emitter of sound (or ultrasonic) waves could be provided. The sensor would then be configured to detect the sound returned from the ice particles in the young contrail.

In an alternative embodiment, the function of the vapour trail detection sensor would be performed by equipment remote to the aircraft, and the resulting information transmitted to the aircraft. Such equipment might include for example sensors mounted on the ground, on airships or balloons, on other aircraft, and/or on earth-orbiting satellites. In such situations, the operation of the non-aircraft mounted vapour-trail detection sensors may optionally be enhanced by use of the aircraft-mounted source of illumination 30.

Figure 2:
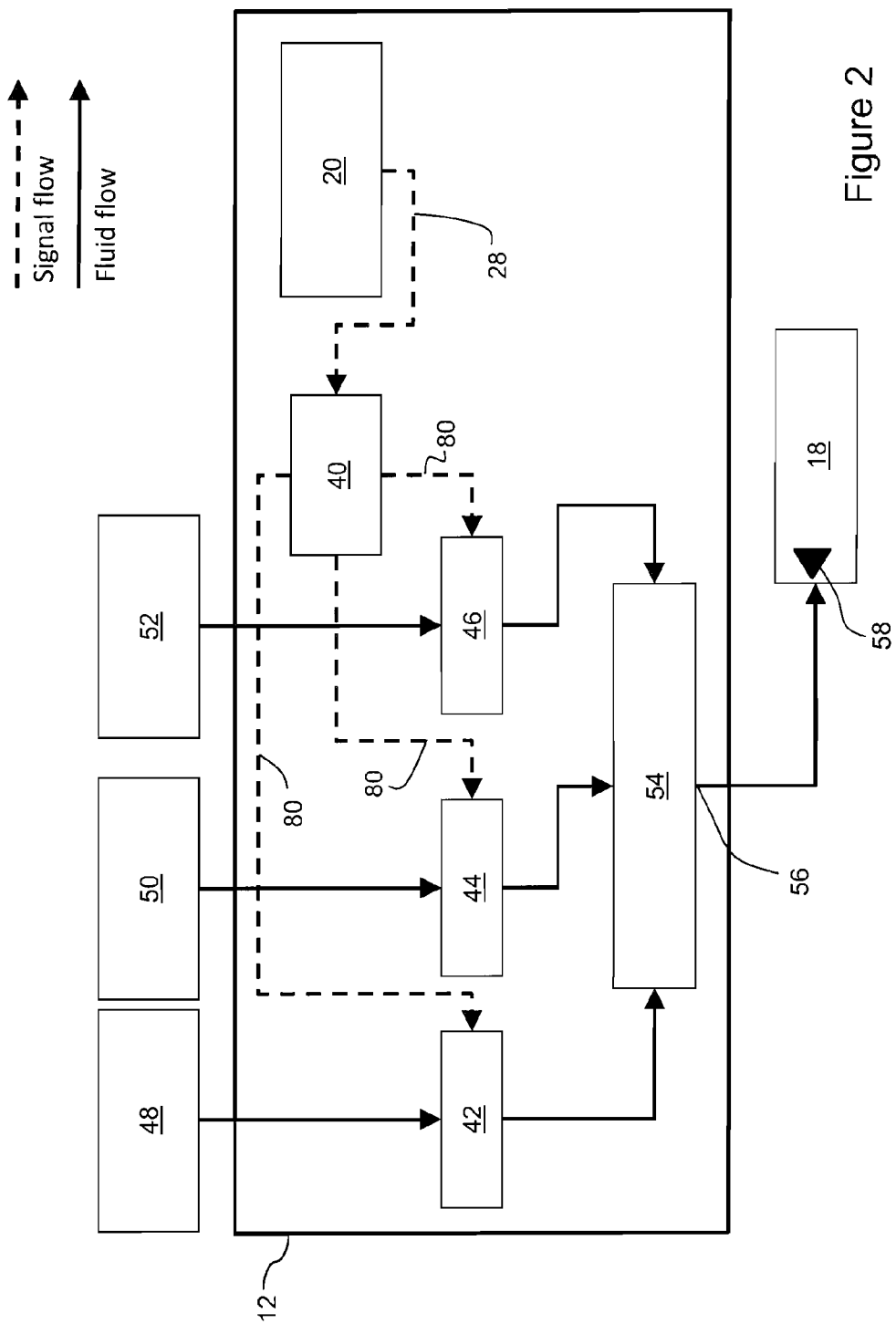
FIG. 2 is a diagrammatic representation of the fuel system of the present disclosure.

FIG. 2 shows a diagrammatic representation of the fuel system 12. For the avoidance of doubt, and as also shown in FIG. 1, the arrows with solid lines indicate the fuel flow communication path, and the arrows with dashed lines indicate signal communication routes.

The fuel system 12 has a control unit 40 which is in signal communication with the or each vapour trail detection sensor(s) 20. In FIG. 2 only one vapour trail detection sensor 20 is shown. In alternative examples there may be more than one sensor 20.

The control unit 40 is also in signal communication with at least a first fuel composition regulator 42 and a second fuel composition regulator 44. In FIG. 2 a third fuel composition regulator 46 is shown. The number of fuel composition regulators is dependent upon the number of fuel compositions the system is configured to operate with. Each fuel composition regulator 42, 44, 46 is in fluid communication with a source 48, 50, 52 of its respective fuel composition. The source of the first fuel composition is a first tank 48 for storage of a first fuel composition, and the source of the second fuel composition is a second tank 50 for storage of a second fuel composition. In the example shown the source of the third fuel composition is a third tank 52 for storage of a third fuel composition. Further tanks are a source of the fuel composition that they are provided to contain. The tanks 48, 50, 52 are located on board the aircraft 10. The tanks 48, 50, 52 etc are fluidly isolated from one another. That is to say, the tanks 48, 50, 52 are not in fluid communication with each other, and there is no flow of fluid between them. The word "tank" is intended to mean an individual tank or a network of fluidly interconnected tanks, where each tank/network is fluidly isolated from the other respective tanks/networks.

The fuel system 12 further comprises a fluid blender 54 in fluid communication with the source 48 of the first fuel composition, the source 50 of the second fuel composition etc via the regulators 42, 44, 46. The blender 54 is configured to mix the first fuel composition, second fuel composition etc to produce a resultant fuel composition.

The fluid blender 54 has at least one outlet 56 for delivering the resultant fuel composition to a fuel injection device 58 in the engine(s) 18. The fuel injection device 58 may be any type of fuel injector, for example a fuel nozzle, airspray injector, or plain orifice. The fuel injection device 58 may comprise one fuel injector, or a plurality of fuel injectors. Although in FIG. 2 and FIG. 3 only one fuel injector 58 is shown, each engine 18 may be fitted with a number of fuel injectors 58, each in fluid communication with the fuel blender 54.

Figure 3:
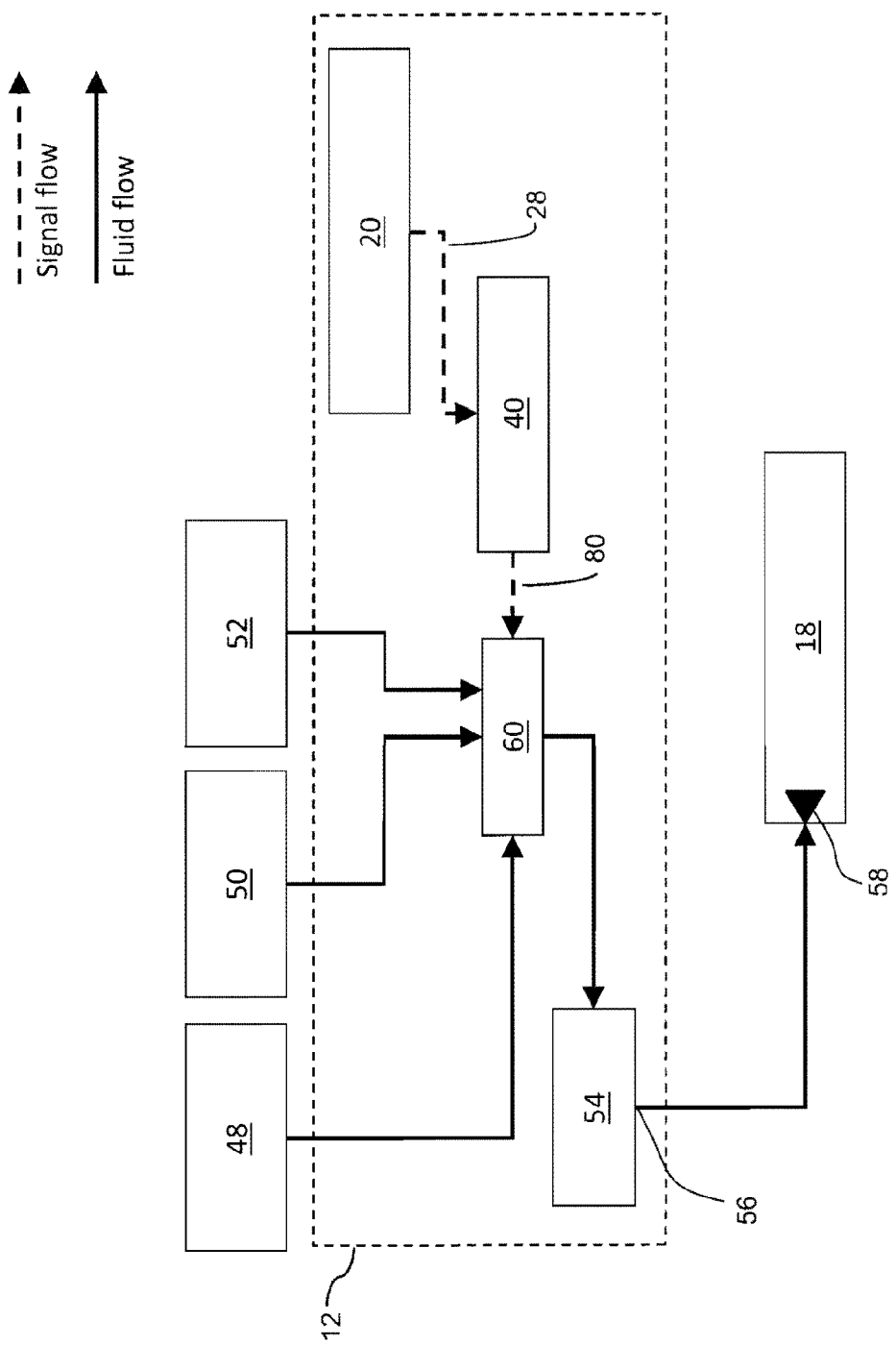
FIG. 3 is an alternative example to that shown in FIG. 2.

FIG. 3 shows a diagrammatic representation of an alternative example of the fuel system 12 according to the present disclosure. Features common to the example shown in FIG. 2 share the same reference numerals. The only difference between the examples is that instead of a regulator 42,44,46 for each fuel composition, there is a single regulator 60 which is in fluid communication with all of the fluid tanks 48,50,52. Such a regulator may thus comprise multiple inlets which are selectively openable and/or closable to control fuel flow therethrough from each, or a combination, of the fuel sources 48, 50, 52.

Figure 4:
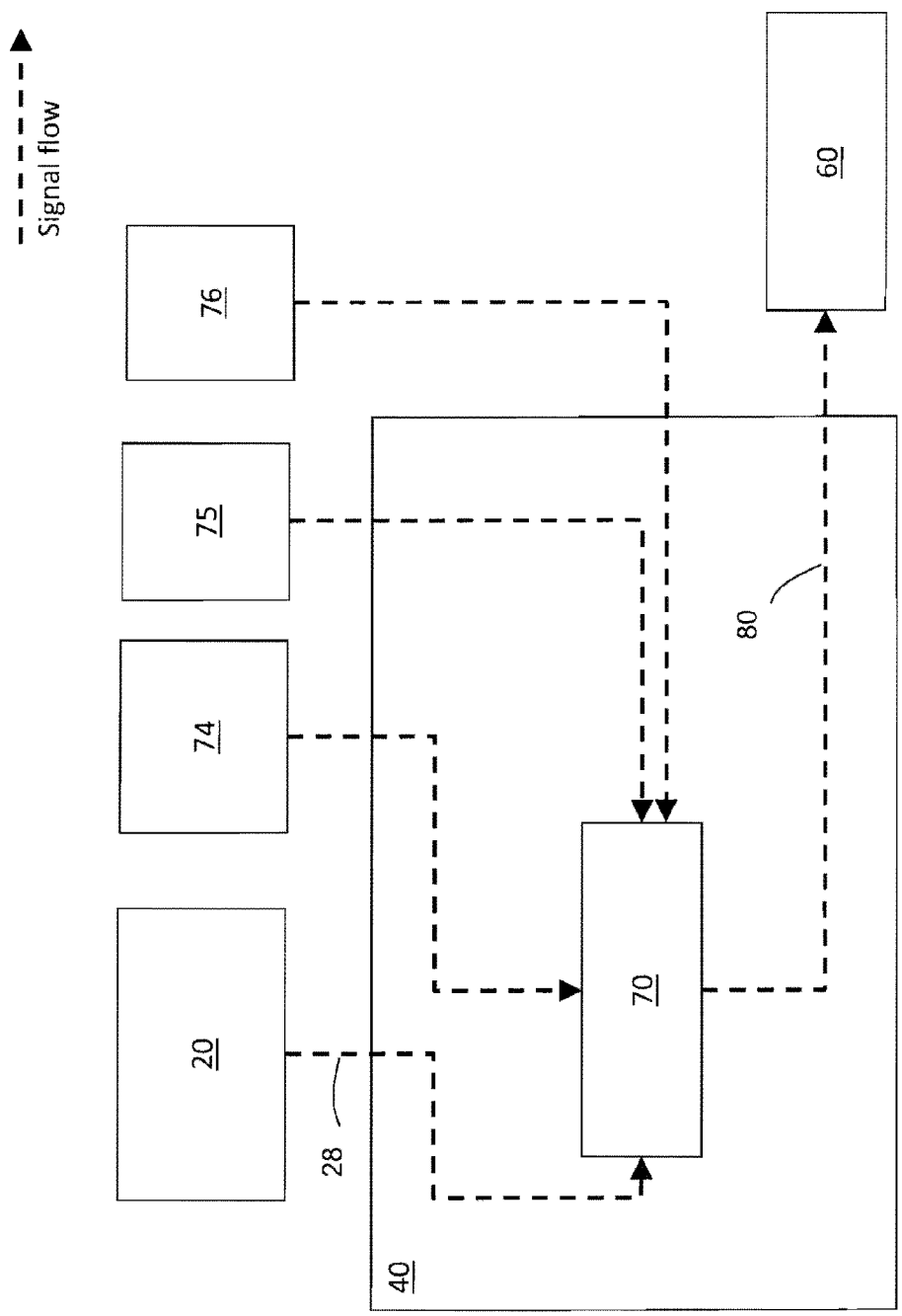
FIG. 4 is a diagrammatic representation showing further detail of the fuel system of the present disclosure.

As shown diagrammatically in FIG. 4, the control unit 40 comprises a blending ratio calculator 70 configured to calculate the required resultant fuel composition. The blending ratio calculator may comprise one or more processors arranged to receive a plurality of inputs and to determine a suitable control output for controlling operation of the regulator 60 of FIG. 3 or else the regulators 42,44,46 shown in FIG. 2 (and possibly the blender 54). It will be appreciated that the control unit 40 may comprise one or a plurality of communicating controllers/processors but will herein be referred to in the singular merely for simplicity.

The control unit 40 is in signal communication with the vapour trail detection sensor 20. It is also in signal communication with one or more ambient temperature sensor 74. In some examples, the control unit 40 may be in signal communication with additional or alternative ambient condition sensors 75 for detecting (e.g. measuring) any of ambient pressure, ambient humidity and/or instantaneous actual values of soot emission index generated by the engine(s) 18. The control unit 40 is also optionally in signal communication with an array of sensors 76 or monitors for determining engine operating point. The engine operating point is defined by a collection of parameters, which may include the ambient conditions in which the engine is operating, comprising one or more engine operation parameter sensor, such as for example one or more sensor for measuring parameters such as fuel-flow rate, operating temperatures and/or pressures of the gas-flow or components at one or more locations on the engine, thrust produced by the engine, engine shaft rotational speed(s) and/or other parameters or settings indicative of the state of the engine.

In each of FIGS. 2-4, numeral 80 indicates a signal representative of the relative proportions of the different available fuels that should be present in the fuel composition to be supplied to the engines. The control signal 80 may define a blending ratio(s) or fuel-flow rates for each of the distinct fluid compositions.

The operation and control of fuel systems in accordance with examples of the invention is described below.

In one example, the blending ratio calculator could comprise a soot requirement generator comprising, or linked to, a look up table or database for determining the desired soot emission index. The look up table or database could thus comprise data relating to the dependency of vapour trail optical depth upon soot emission index at various ambient conditions. Alternatively, or additionally, the soot requirement generator comprises a model and/or algorithm for direct calculation of the desired soot emission index. However it has been determined that the use of such a method alone could result in a system which is inoperable or sub-optimal for a number of scenarios. More specifically, such a system would be dependent on a number of sources of data in order to operate effectively, including sensor data and computational models or look-up tables. For example failure of an ambient temperature sensor, could lead to an inability to identify the currently optimal soot emission index and/or failure of one or more of the engine operating point sensors could lead to an inability to calculate the fuel blend ratio required to achieve the target soot emission index. Incomplete, insufficiently accurate knowledge of the compositions of the fuels available for blending or algorithms, computational models, lookup-tables or databases describing the relationships between fuel blending, soot emission index and contrail optical depth could also lead to ineffective system performance.

Accordingly a control scheme for use as an alternative to, or else in combination with, such methods is described in further detail below with reference to FIGS. 5 to 8.

Figure 5:
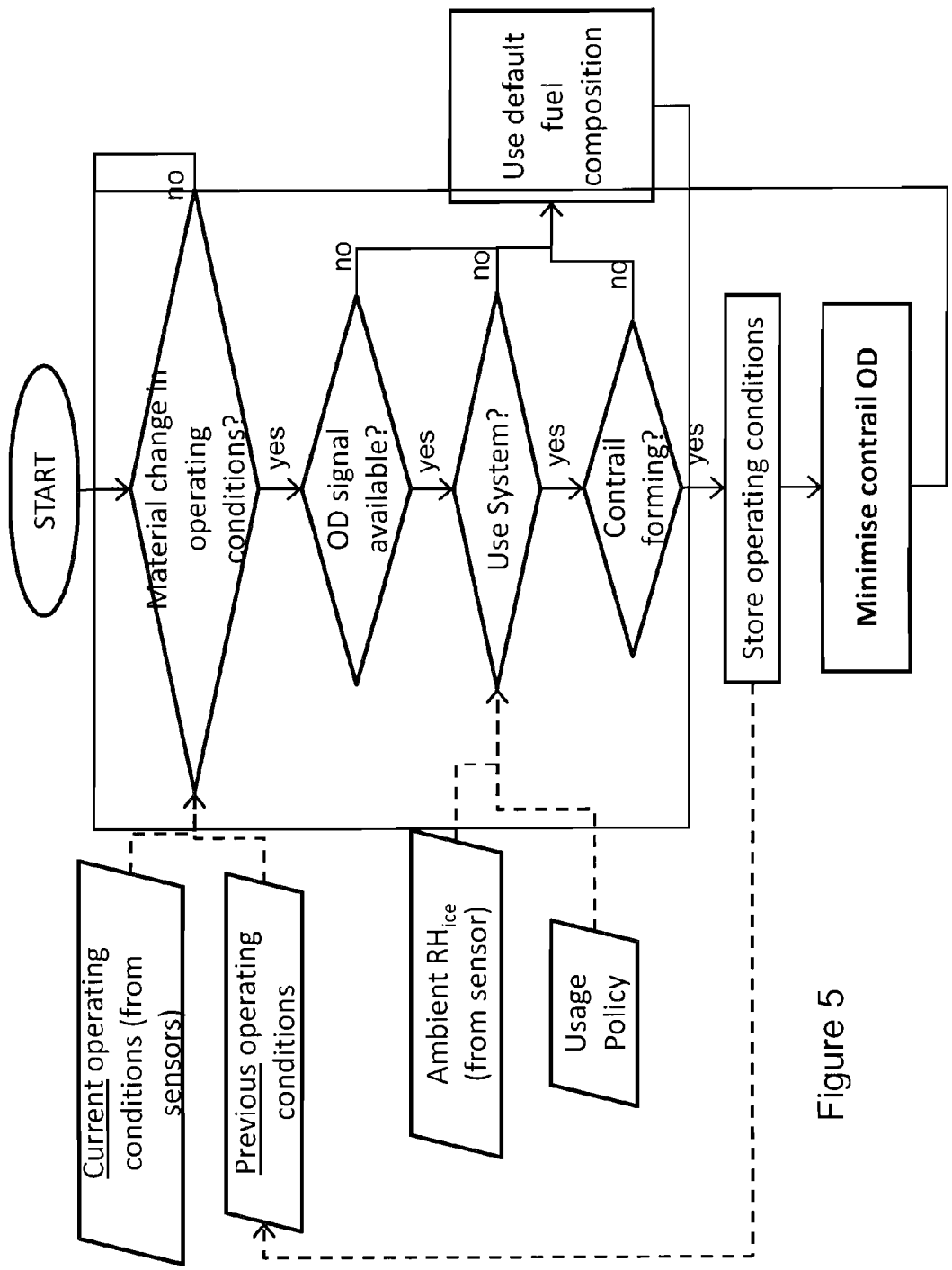
FIG. 5 is a flow chart showing the operation of a system according to an example of the invention.
Figure 6A:
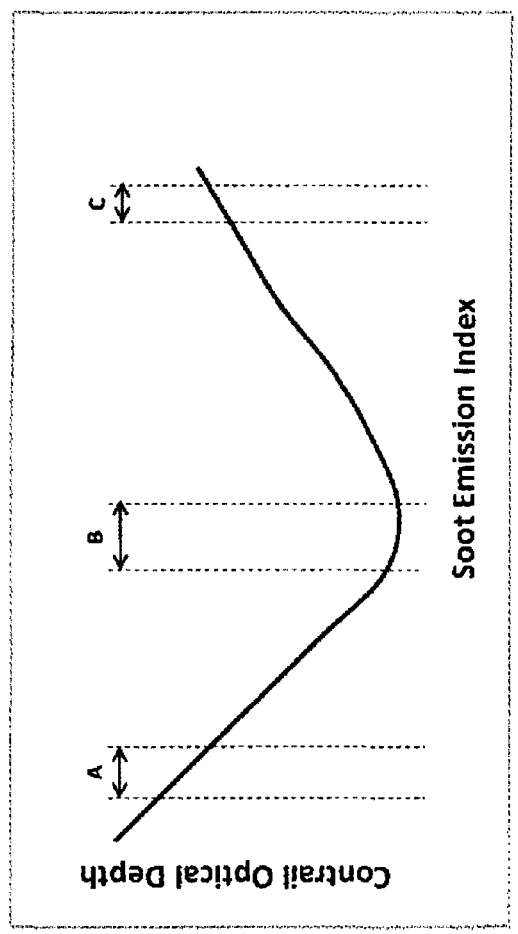
FIGS. 6A and 6B show plots of contrail optical depth against soot emission index for examples of regimes identified according to an example of the invention.
Figure 6B:
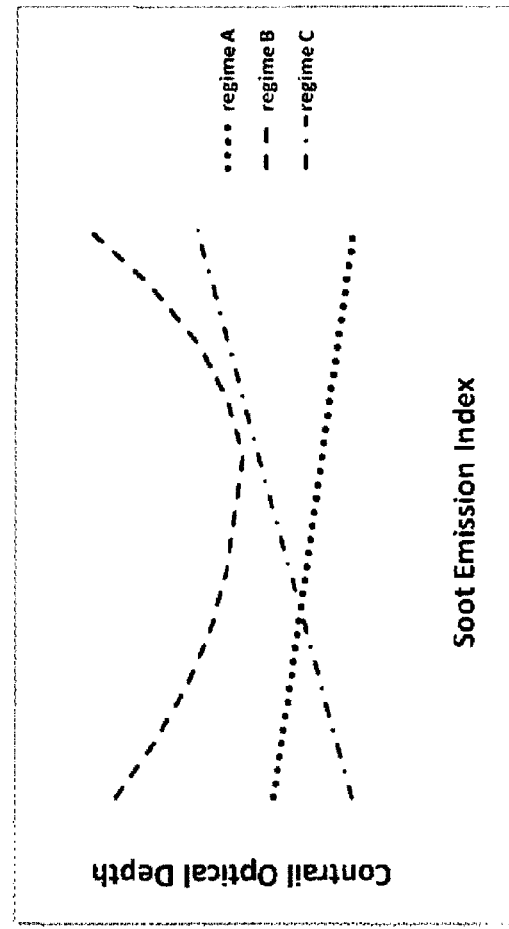
Figure 7:
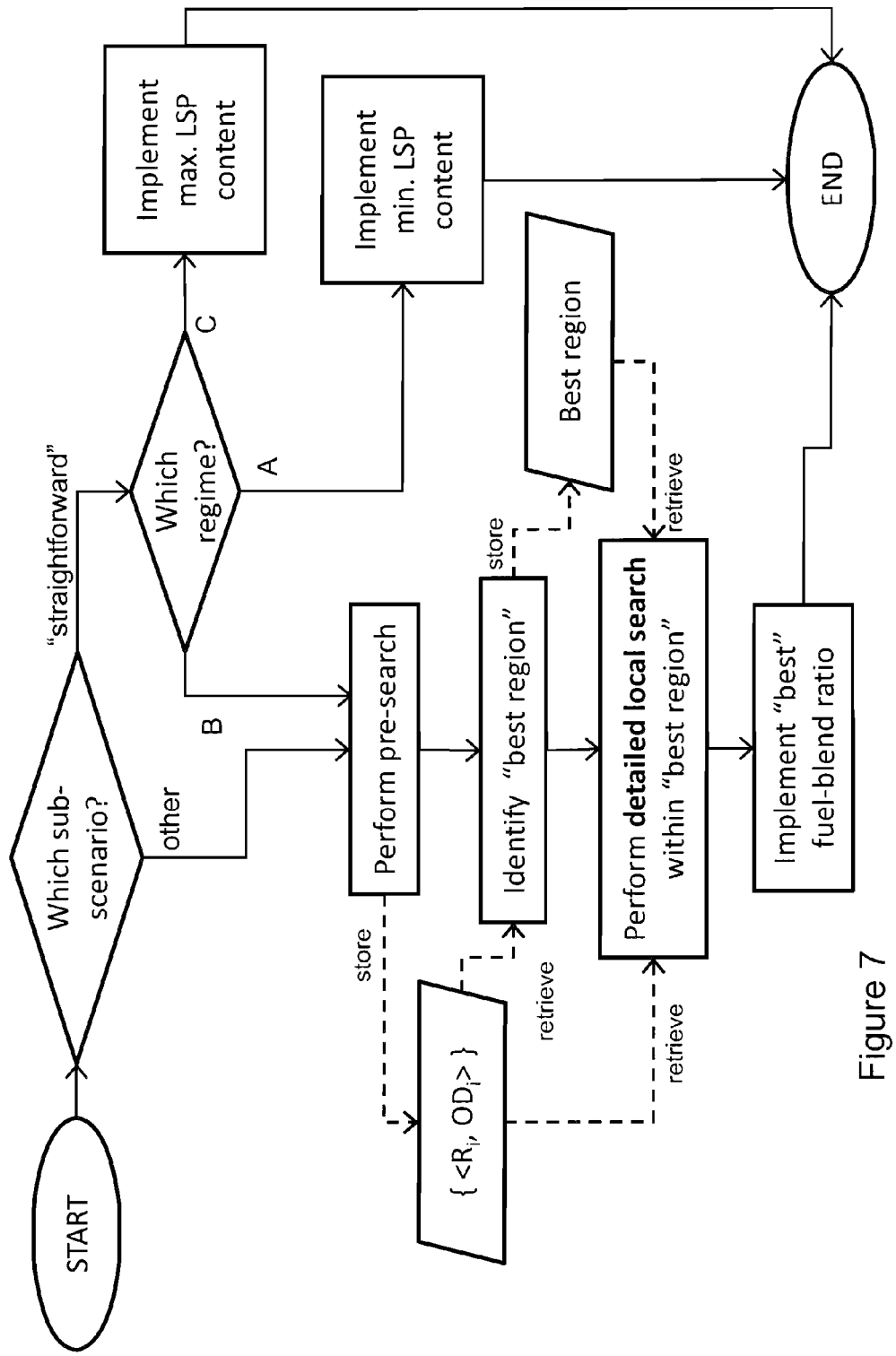
FIG. 7 is a flow chart of the operation of a fuel system to manage contrail formation according to the invention; and, FIG. 8 is a flow chart of an operation to fine tune control of the fuel system for contrail reduction.

Turning firstly to FIG. 5 there is shown a high level decision-making process for determining whether control steps are required to mitigate against contrail formation. The control system operates a primary loop to check whether the operating conditions (i.e. the ambient conditions and/or engine operation parameters) have changed materially since a previous iteration. The operating conditions could comprise any, or any combination of, ambient temperature, ambient pressure, ambient humidity, altitude, and/or engine throttle setting. This primary loop can be iterated without changing existing settings until a relevant change to operating conditions is determined.

The controller then determines whether the vapour trail detection sensor 20 (e.g. contrail optical depth (OD) sensor) is working correctly and is able to provide a signal indicative of the OD of any contrail which may form. If so, a usage policy may optionally be employed to determine whether it is deemed appropriate to use a method for controlling the fuel composition delivered to the engine according to the invention under the current operating conditions. For instance, it may or may not be considered appropriate to only use this invention when contrails persist, e.g. if ambient relative humidity over ice is 100% or greater. Additionally or alternatively, it may be deemed inappropriate to use the invention if engine operating conditions or external requirements restrict the available fuel compositions. Additionally or alternatively, the decision to use or not to use this invention to modify contrail properties may be informed by other factors such as the ambient temperature and/or the strength of incoming sunlight incident upon the formed contrail. For example, it may be deemed appropriate to attempt to ameliorate only contrails which are both persistent and existing primarily during the night-time. Such additional decision criteria would allow scarce and expensive biofuels to be targeted specifically at contrails with the highest climate-warming impact. Accordingly it is possible that an ambient condition sensor could comprise a light sensor.

An assessment of whether or not a contrail is forming is undertaken, for example by comparing the measurement of vapour trail detection sensor 20 (e.g. contrail OD) against a pre-determined threshold value. It is envisaged that it would be possible to choose a suitable threshold value that lay well below the minimum likely contrail OD achievable through the operation of the invention, thus avoiding rapidly-cycling intermittent operation of the invention. Alternatively a zero threshold could be used. In either example, the duration for which the threshold is exceeded may be taken into account and the fuel composition control scheme delayed accordingly.

If there has been no material change in the operating conditions, then the current fuel composition is retained. If a material change in the operating conditions is detected but any of the other conditions described above are not satisfied, then a default fuel composition is used. For example in the absence of vapour trail formation, it may be desirable to use only one of the first or second fuel compositions, and hence the resultant fuel composition will simply be the first or second fuel composition. For example 100% kerosene may be delivered to the engines 18 via the fuel injectors 58, rather than a blend of kerosene and biofuel. Alternatively where the ambient conditions are such that vapour trails form but do not persist (i.e. in ambient air not super-saturated with respect to ice), the system could be operated or not operated, depending on the extent to which the occurrence of temporary vapour trails is considered desirable or not, and taking account of the available quantity of biofuel.

If all conditions are satisfied then a control scheme according to the invention, typically involving a search algorithm (or a simpler alternative where appropriate, as discussed below), is invoked to determine and implement the best fuel-composition for the prevailing conditions.

The control methods according to the examples below are based upon an understanding that contrail optical depth (OD) will vary with soot emission index (EI), as follows:
1) for a certain range or ranges of ambient temperatures, reducing soot EI—from that typically observed at cruise conditions—results in a reduction of contrail OD within a particular range of soot EI considered; and, 2) for other ranges of ambient temperature, there is a minimum point in the dependency of contrail OD upon soot EI. This means that as soot EI is reduced (from values typically observed at cruise conditions), contrail OD falls but then at some point starts to rise again, as the significance—for ice particle formation—of soot particles originating from the engine exhaust starts to fall below that of ambient particulates and/or non-soot exhaust components (such as sulphur).

In the general case, one can expect a trough-shaped dependency of contrail OD spanning a certain range of soot EI as shown in FIG. 6A. However, the range of soot EI that can be achieved in practice is likely to be limited by a number of factors, such as: the engine's current operating point, including ambient conditions as well as absolute limits, technical, regulatory or commercial constraints on the range of possible useable fuel blends.

Thus it has been determined that the engine can beneficially be characterised as operating in one of a plurality of regimes for the purpose of the invention. Three broad regimes—regime A, regime B or regime C, illustrated in FIG. 6, are used in this example although other subdivisions may be appropriate in alternative embodiments. Regimes A and C approximate a generally linear relationship (respectively descending and ascending) between contrail OD and soot EI. Alternatively, regimes A and/or C could each approximate another simple non-linear mathematical relationship in which the gradient does not change sign (e.g. monotonically increasing or decreasing). Regime B assumes contrail OD will tend to a local or absolute minimum value for a given soot EI but will increase on either side thereof.

Options for identification of the different regimes A, B and C include on-board computation, pre-populated lookup-table or database, or a decision-tree. Ambient temperature and soot EI could be used as the major contributing factors for determining the current regime.

Turning to FIG. 7, there is shown the methodology or framework for altering the fuel blend delivered to the combustor by use of a search strategy. That is to say, the system may implement one or more attempts at a desired fuel blend and may monitor the impact on vapour trail formation in order to allow iteration towards an optimal final fuel composition for the current ambient/operating conditions.

If it is determined that the engine is operating in regime B, a search algorithm could be employed to find the optimum soot EI which corresponds to lowest contrail OD as will be described below. However, under certain circumstances, it may be possible to identify with an adequate level of certainty that the operating regime is in fact regime A or alternatively regime C. Under those circumstances, the task of the search algorithm is potentially simplified, since all that is required is to choose the maximum achievable or minimum achievable soot EI. Thus different embodiments of the invention may or may not include the regime/scenario identification stage at the start of the flow chart of FIG. 7.

In addition to the correlating of contrail OD with soot EI shown in FIG. 6, there is another mapping or relationship that must be taken into account, namely that between fuel blend ratio and soot EI. Thus a preliminary decision is taken in the process shown in FIG. 7, i.e. prior to regime selection, in order to identify a scenario of operation based upon fuel blend/soot EI mapping. A number of scenarios are considered here:

The simplest case is one in which only two fuel compositions are available for mixing so as to tune the soot EI. For example the two fuel compositions might be a low-soot-producing (LSP) fuel and kerosene. An LSP fuel might be for example a biofuel or gas-to liquids (GTL) or alternatively some other form of synthetic kerosene. In this example, there are 2 sub-scenarios:

i. In the first sub-scenario, the dependency of soot EI upon LSP-fuel content within the blend is such that increasing the percentage of LSP fuel will not result in an increase in soot EI. That is to say, if a fuel blend consisting of x % LSP-fuel and (100−x) % kerosene can be described as Lx, then we have sootEI(Ly)<=sootEI (Lx), for all y>x within the allowable/achievable range of fuel blends. This sub-scenario also subsumes the case where soot EI is a monotonically decreasing function of increasing LSP-fuel percentage in the blend, in which case we would have sootEI(Ly)<sootEI (Lx) for all y>x. This sub-scenario is considered the most likely and is identified in FIG. 7 as the "straightforward" case, thus leading to a regime selection as described above.

ii. Alternatively, the dependency of soot EI upon LSP-fuel percentage might be such that for some ranges of LSP-fuel content, further increases result in a higher sootEI. That is to say that, for some values of x and y within the permissible range, if y>x we have sootEI(Ly)>sootEI (Lx). This sub-scenario is considered less likely but could be relevant as different fuel blends are explored for aviation. Accordingly the scenario selection stage may be omitted in other embodiments of the invention as necessary.

In another example in which there are more than two fuel compositions available for blending, the search for the ideal fuel blend is therefore multi-dimensional. In such an example the sub-scenarios set out above concerning the dependency of soot EI upon LSP-fuel percentage within the blend may or may not be assessed.

In the "straightforward" case above the process can then move on to regime selection. For regimes A or C, it is possible simply to choose a fuel blend ratio corresponding to the minimum (for regime A) or maximum (for regime C) LSP-fuel percentage achievable or allowable.

However, in the general case of regime B (or the other sub-scenario, e.g. coupled with regime A or C), a search algorithm (also known as a function optimisation algorithm or "optimiser") is used to explore the search space defined by various blending ratios of the individual fuel compositions. The search algorithm may also be applied as a default option, for example if it is not possible to rule out regime B with an adequate degree of certainty, e.g. if regime A or C cannot be determined, and/or if the ambient temperature sensor reading is defective, or if the relationship between contrail OD and soot EI is uncertain for any other reason at the given conditions. Other embodiments may not apply the steps of distinguishing between regimes and/or scenarios of operation, and may use a search algorithm in all cases. Alternatively another embodiment may apply only a regime determination stage in order to allow identification of simple regimes for which a search algorithm is not required, i.e. in which an optimal fuel blend can be selected with certainty.

For one or more of the above described embodiments, there will exist operating conditions for which a search algorithm is to be employed. The algorithm allows the fuel blend to be varied in a controlled manner so as to determine the effect of the attempted fuel blend variation on contrail formation, e.g. by measuring contrail OD using sensor 20 or another characterising property of the contrail. The manner in which the fuel blend is varied and the resulting impact on the engine exhaust emissions is determined (i.e. the search algorithm) may be subject to various options.

Figure 8:
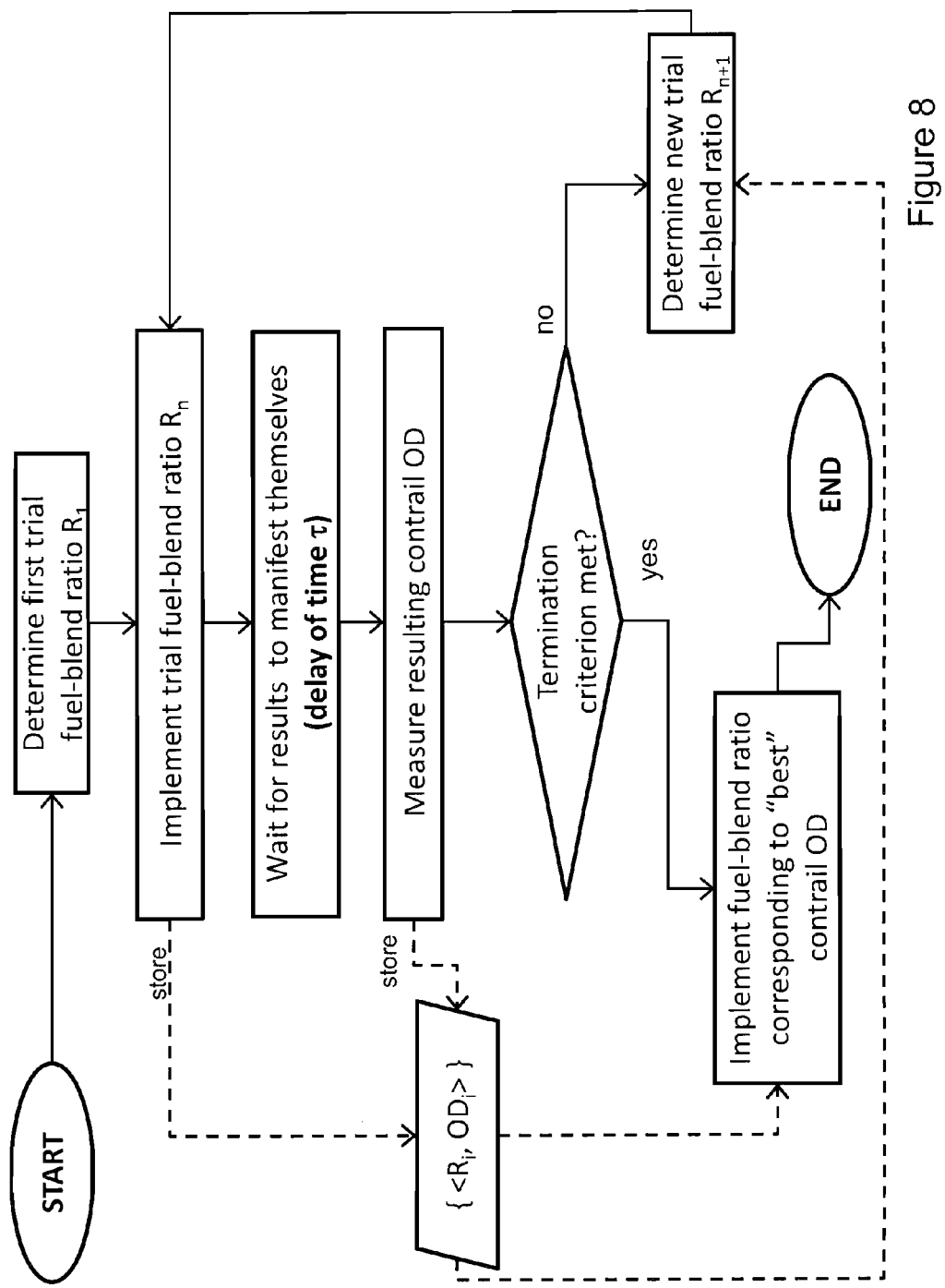

For any search algorithm, it is important to note that there is an inherent delay in the system between the point in time at which a particular fuel-blending ratio is instructed, and the point at which the resulting contrail characteristic (e.g. the optical depth reading) for that fuel blend is available to the control unit. This delay relates to the time taken: for actuation of the regulator valves; for fuel to travel along fuel-lines; to mix the individual fuel compositions in the blender; for combustion; for the contrail to form and exhibit properties related to the chosen fuel composition; and time taken to assess suitability of trial fuel blend, i.e. to measure the contrail property with the required certainty and communicate/process the results at the controller. This delay is referred to as the contrail lead-time, $\tau$. The contrail lead-time limits the number of trial fuel compositions that can be explored per unit time, when using a search algorithm which waits for the results of a function evaluation before deciding what combination of parameter values to try next. Such delays are undesirable, particularly for aircraft travel velocities and so it is generally desirable to adopt a search algorithm or methodology which requires a minimum number of iterations or time delay to find an optimum fuel-blend.

In the example described below, it is proposed to perform a pre-search or sweep of the available fuel blend range, thereby incurring the contrail lead-time delay only once for the entire range. That is to say because a decision is not taken after each and every function evaluation, the entire range can be swept and the effects on contrail suppression recorded for the entire swept range, i.e. effectively performing a number of function evaluations in a single sweep. The pre-search may thus return an approximate range in which the fuel blend is optimal. A more accurate determination of the precise optimal fuel blend may then be run within the identified region, for example using a second/local search algorithm. In examples of the invention either one of the pre-search or second search algorithms may be used exclusively.

Since the contrail lead-time is independent of fuel-blend ratio, and depends only upon the rate at which fuel is supplied to the engine, then it can be characterised with reasonable accuracy. This means that a measurement of contrail OD observed at any particular time t can be attributed to a fuel-blending ratio instruction in operation at time $t-\tau$ The different possible algorithms that could be employed thus may comprise any or any combination of:

1. A continuous sweep of the full range of achievable fuel-blend ratios, using knowledge of the contrail lead-time, so as to be able to quickly identify the fuel-blend ratio corresponding to the minimum contrail OD observed during the sweep. This may be considered equivalent to a continuous pre-search covering the entire range of achievable fuel-blend ratios. Such an approach is feasible in very low-dimensional search spaces, e.g. if there were only two fuel compositions (in which case the search would be one-dimensional).

2. An optimisation algorithm (i.e. secondary search) coupled with a pre-search consisting of a small number of discrete sample points within the search space. The results of the pre-search can then be used to bound the optimisation algorithm to a sub-region of the overall search space in order that the optimisation algorithm converges on an optimal value more quickly, thereby reducing the total environmental impact of the trial solutions explored. It may also reduce the total number of function evaluations required by the search algorithm.

One possible search algorithm may comprise, for example, Nelder & Mead's "downhill simplex" method, although other conventional or bespoke algorithms may prove suitable. Methods not requiring computation of the gradient of the fitness function may have an advantage in this application. In all examples of a function optimisation algorithm (or "optimiser"), a search is performed for a final fuel composition which corresponds to substantially the minimum achievable contrail OD, given the current engine operating point and ambient conditions and any constraints imposed by the range of final fuel compositions which can be implemented in practice.

Additionally or alternatively, a search is performed for a final fuel composition representing the most desirable balance between the cost of the final fuel composition and any avoided cost relating to the reduced optical depth of the contrail. Optionally, when determining the cost of the final fuel composition, any potential variations in additional charges, such as those related to carbon dioxide emissions, are also taken into account.

One key characteristic of the pre-search phase described above is that the selection of points to be explored is determined 'a priori' and is not influenced by the values of contrail OD measured during the pre-search so as to avoid substantial time delays. Thus each successive fuel blend ratio can be instructed while the consequences of the previous one are still propagating through the fuel system. However, a short holding time for discrete ratios attempted may be applied in order to help delineate between each condition to be sampled. The required duration of holding time may be predetermined based at least in part on the known contrail lead-time tolerance and/or any recorded variation in contrail lead-time over the course of a single flight, between flights, or between different aircraft of the same design. In any event, it is envisaged that the holding time will be significantly smaller in magnitude than the contrail lead time. For a continuous sweep, the rate of change of the fuel blend may be tailored to avoid the need for a holding time or else a shortened holding time may be applied at discrete intervals.

In any of the search examples described above, a first step of the search may comprise a determination of a list of points (i.e. fuel blend ratios) to be explored within the search space. This can be done by evenly distributing a given number of points across an N-dimensional space. Another (although typically less efficient for two or higher search dimensions) approach would simply be to identify points lying on regular grid whose axes lie parallel to the axes of the search space.

The above described approaches may be considered to enable a "pipeline" approach to characterising the particular relationship—applying specifically at the prevailing ambient conditions and engine operating point—between fuel-blend ratio and contrail OD. The pipeline approach can be implemented in a discrete or continuous mode.

FIG. 8 illustrates an optimisation loop for detailed local search in which the delay τ is incurred for each evaluation of a trial fuel-blend ratio, thereby requiring the outcome of one fuel blend ratio, Rn, to be determined before making a decision concerning the next trial fuel-blend ratio, Rn+1, to be attempted after ratio Rn. That is to say, the next trial fuel blend ratio is determined in dependence upon the results of the measurement of optical depth, ODn, corresponding to the previous or current ratio, Rn.

In one example of the invention the control unit may implement either a pre-search or optimisation search algorithm selectively in dependence upon the magnitude in a change in ambient conditions or engine operating conditions. Thus a sweep search may be avoided for only small changes in operating point.

The search strategies according to examples of the invention allow a simple but robust method of determining an optimal fuel-blend ratio for varying operating conditions. The techniques described above rely on a relatively small set of input parameters, and so have fewer possible sensor-related failure modes, whilst also avoiding the need to have available wholly accurate models, algorithms, lookup-tables or databases concerning the relationship between soot emission index and contrail optical depth, or concerning the relationship between fuel-blend ratio and soot emission index. However, if such information is available, it can be employed in conjunction with the search techniques described above to identify cases in which a more efficient approach can be taken. Furthermore the invention could react to changes in the fuels used or incorrect fuel loading, e.g. where there is uncertainty over the fuel compositions in each tank.

In the context of the present disclosure, "optimal" soot emission index is the soot emission index which, if realised in practice under the prevailing ambient conditions, would lead to a minimisation of optical depth of the young contrail, and hence a minimisation of a young contrail's climate warming impact. Under some ambient conditions the "optimal" soot emission index may correspond to the minimum achievable soot emission index given the available fuels and any constraints that may place limits on the blending ratios that may be employed. Alternatively, under other ambient conditions, the "optimal" soot emission index may be higher than or lower than the minimum achievable soot emission index.

The first fuel composition may have an aromatic and/or other non-paraffinic content substantially higher than that of the second fuel composition. In one example the first fuel composition is Kerosene. Additionally or alternatively the second fuel composition is a biofuel. The second fuel composition may be a low-soot-producing (LSP) or alternatively a low-sulphur, low-soot-producing (LSLSP) fuel. Alternatively or additionally the second fuel may be a blend of several such LSP and/or LSLSP fuels whose physical and chemical properties make it suitable for use in an engine with the first fuel composition, for example as an aviation fuel when blended with conventional kerosene. Examples include (but are not limited to) coal-to-liquids (CTL), gas-to-liquids (GTL), biomass-to-liquids (BTL), synthetic paraffinic kerosene (SPK), hydrotreated renewable jet-fuel (HRJ), alcohol-to-jet, and Hydro-processed Esters and Fatty Acids (HEFA).

Alternatively, the second fuel composition could be liquefied natural gas (LNG) or hydrogen. In such cases, the first and second fuel compositions may require separate injection mechanisms into the engine, and so blending or mixing may not take place prior to injection into the engine, but may instead occur for example within the turbulent environment of the engine's combustion chamber.

The system 12 is operable to blend fuel, or to simply deliver one of the stored fuel compositions. That is to say the action of blending together two or more fuels may optionally be employed or not employed according to policy decision taking account of ambient conditions and engine operating point. The resultant fuel composition may comprise any proportion of first fuel composition and second fuel composition in the range from 0% to 100%. The resultant fuel composition may comprise x % of the first fuel composition and (100−x) % of the second fuel composition, where x has a value anywhere in the range from 0 to 100. For example, the resultant fuel composition may comprise 0% of the first fuel composition and 100% of the second fuel composition. Alternatively the resultant fuel composition may comprise 100% of the first fuel composition and 0% of the second fuel composition. Additionally x may have a value greater than 0 and less than 100. In an alternative example the resultant fuel composition may comprise a % of the first fuel composition, b % of the second fuel composition and c % of additional fuel or additive compositions, where a+b+c=100%, and a, b or c may have a value anywhere in the range from 0 to 100%.

The control unit 40 may determine which of a default fuel composition and a composition which may enable the optical depth of the vapour trail to be reduced is employed. This determination may be based on the determined likelihood of contrail formation and/or persistence, and taking into account an operational policy specifying the conditions under which vapour trail optical-depth modification should be attempted.

Advantageously, this invention incurs very little weight penalty and it also requires very low energy to operate. Furthermore the invention does not interfere with engine operating point and does not introduce a significant fuel-efficiency penalty or present lifting issues for the engine to be able to accommodate contrail reduction. Also the invention could reduce and/or avoid the need to navigate around regions of ice-supersaturated air, thereby avoiding fuel burn penalties and allowing aircraft to adopt an optimal cruise trajectory while still benefitting from a material reduction in overall climate impact.

According to aspects of the invention, each time the system determines that a change in fuel composition is required relative to the fuel composition currently/previously supplied to the engine, a controller may determine a difference in specific energy between the current and new/proposed fuel compositions. If a difference is determined, the controller may output control instructions to adjust the flow rate of the proposed/new fuel composition, e.g. relative to the current composition flow rate, when delivered to the engine to maintain the same rate of fuel energy input to the engine. Thus the same level of thrust can be delivered by the engine despite the change in fuel composition being supplied. Whilst the changes in specific energy by use of the invention are envisaged to be relatively small, such a check may be important in assuring safety and predictable ongoing engine operation. Accordingly such a feature may be generally applicable to any of the embodiments described above.

The invention claimed is:

1. A fuel delivery system for an engine, the system comprising:
   a vapour trail detection sensor configured to generate a detection signal indicative of a characteristic of a vapour trail;
   a regulator configured to regulate a volume of a first and a second fuel composition delivered to the engine as resultant fuel composition; and
   a controller arranged to undertake a search of trial fuel compositions by controlling the regulator to deliver to the engine a plurality of trial fuel compositions having different ratios of the first and second fuel compositions and to control delivery of a resultant fuel composition to the engine in response to the vapour trail characteristic detection signals for said plurality of trial fuel compositions, wherein the search comprises a first coarse search to identify a sub-range or point for which a desirable value of the vapour trail characteristic is sensed, and a second search which identifies an optimal final fuel composition in the vicinity of said sub-range or point.

2. The fuel delivery system according to claim 1, wherein the first coarse search is conducted according to a predetermined routine.

3. The fuel delivery system according to claim 1, wherein the second search is iterative, each iteration of a trial fuel composition ratio being dependent on a vapour trail detection sensor signal corresponding to one or more previous trial fuel composition ratios.

4. A fuel delivery system for an engine, the system comprising:
a vapour trail detection sensor configured to generate a detection signal indicative of a characteristic of a vapour trail;
a regulator configured to regulate a volume of a first and a second fuel composition delivered to the engine as resultant fuel composition; and
a controller arranged to undertake a search of trial fuel compositions by controlling the regulator to deliver to the engine a plurality of trial fuel compositions having different ratios of the first and second fuel compositions and to control delivery of a resultant fuel composition to the engine in response to the vapour trail characteristic detection signals for said plurality of trial fuel compositions.

5. The fuel delivery system according to claim 4, wherein the controller comprises a search algorithm arranged to perform a sweep through a range of fuel composition ratios upon detection of a change in one or more conditions including an engine operating condition and an ambient condition.

6. The fuel delivery system according to claim 5, wherein the ambient condition comprises at least one of the sensed vapour trail characteristic, the ambient temperature, and humidity.

7. The fuel delivery system according to claim 5, wherein the sweep comprises a continuous sweep through the range.

8. The fuel delivery system according to claim 5, wherein the sweep comprises a sweep through a plurality of discrete fuel composition ratios across the range.

9. The fuel delivery system according to claim 4, wherein in addition to the search, the controller is arranged to refer to a predetermined data array including at least one of a database, a lookup-table, a decision-tree and an algorithm, in determining the resultant fuel composition for delivery to the engine.

10. The fuel delivery system according to claim 4, wherein the system comprises one or more sensors including an ambient condition sensor and an engine operation sensor, and the controller is arranged to identify an engine operation regime based at least in part upon readings from the one or more sensors.

11. The fuel delivery system according to claim 10, wherein a plurality of regimes are defined, each of which having a different predetermined relationship between the vapour trail characteristic and the sensed parameter, the controller determining whether or not to perform the search based upon said regime determination.

12. The fuel delivery system according to claim 10, wherein the engine operating regime is characterised at least in part based on a relationship between fuel composition ratio and the sensed engine operation parameter, the controller determining whether or not to perform the search based upon said regime determination.

13. The fuel delivery system according to claim 10, wherein the engine operation parameter comprises a soot emission index.

14. The fuel delivery system according to claim 4, wherein the controller selects a final fuel composition ratio so as to minimise vapour trail optical depth.

15. The fuel delivery system according to claim 4, further comprising first and second fuel tanks, each tank being fluidly isolated from the other, wherein the first fuel tank contains the first fuel composition and the second fuel tank contains the second fuel composition, each tank having an associated regulator for controlling the delivery of said respective fuel to the engine.

16. The fuel delivery system according to claim 4, wherein the regulator comprises a fuel blender arranged to receive the first and second fuel compositions and to output a final fuel composition comprising a substantially homogeneous mixture of the first and second fuel compositions to the engine.

17. An aircraft comprising a fuel delivery system according to claim 4.

18. The fuel delivery system according to claim 4, wherein the vapour trail detection sensor comprises an optical sensor.

19. A fuel delivery method for an engine comprising:
receiving a vapour trail detection signal indicative of a characteristic of a vapour trail produced by the engine;
regulating a volume of a first and a second fuel composition delivered to the engine as resultant fuel composition; and
undertaking a search of trial fuel compositions by controlling delivery to the engine of a plurality of trial fuel compositions having different ratios of the first and second fuel compositions and
controlling delivery of a resultant fuel composition to the engine in response to vapour trail characteristic detection signals for said plurality of trial fuel compositions.

20. A data carrier comprising non-transitory machine readable instructions for the operation of an engine fuel system controller to control delivery of first and second fuel compositions to an engine by:
receiving a vapour trail detection sensor signal output and to determine the presence or absence of a vapour trail caused by an engine exhaust flow;
upon detection of a vapour trail undertaking a search of trial fuel compositions having different ratios of the first and second fuel compositions by controlling delivery of said trial fuel compositions to the engine;
controlling delivery of a resultant fuel composition to the engine in response to vapour trail characteristic detection signals for said plurality of trial fuel compositions.

* * * * *